United States Patent
Yamashita et al.

(10) Patent No.: US 11,407,826 B2
(45) Date of Patent: Aug. 9, 2022

(54) SCREENING METHOD FOR PAIN SUPPRESSOR AND PHARMACEUTICAL COMPOSITION FOR PREVENTION OR TREATMENT OF PAIN

(71) Applicant: Osaka University, Osaka (JP)

(72) Inventors: Toshihide Yamashita, Osaka (JP); Yasufumi Hayano, Osaka (JP); Moe Yamada, Osaka (JP)

(73) Assignee: Osaka University, Osaka (JP)

( * ) Notice: Subject to any disclaimer, the term of this patent is extended or adjusted under 35 U.S.C. 154(b) by 227 days.

(21) Appl. No.: 16/802,258

(22) Filed: Feb. 26, 2020

(65) Prior Publication Data
US 2020/0190184 A1 Jun. 18, 2020

Related U.S. Application Data

(62) Division of application No. 15/542,859, filed as application No. PCT/JP2016/053919 on Feb. 10, 2016, now Pat. No. 10,611,834.

(30) Foreign Application Priority Data
Feb. 13, 2015 (JP) ................. 2015-025954

(51) Int. Cl.
| | |
|---|---|
| *C07K 16/28* | (2006.01) |
| *A61K 38/00* | (2006.01) |
| *A61K 39/395* | (2006.01) |
| *C12N 15/113* | (2010.01) |
| *G01N 33/50* | (2006.01) |
| *A61K 39/00* | (2006.01) |
| *A61K 45/00* | (2006.01) |
| *C12Q 1/6883* | (2018.01) |

(52) U.S. Cl.
CPC .............. *C07K 16/28* (2013.01); *A61K 38/00* (2013.01); *A61K 39/395* (2013.01); *A61K 45/00* (2013.01); *C12N 15/1138* (2013.01); *C12Q 1/6883* (2013.01); *G01N 33/5023* (2013.01); *G01N 33/5058* (2013.01); *A61K 2039/505* (2013.01); *C07K 2317/76* (2013.01); *C12N 2310/14* (2013.01); *C12Q 2600/136* (2013.01); *C12Q 2600/158* (2013.01); *G01N 2333/705* (2013.01)

(58) Field of Classification Search
CPC ............ C12Q 2600/158; C12Q 1/6883; C12Q 2600/136; G01N 33/5023; G01N 2333/705; G01N 33/5058; A61K 38/00; A61K 39/395; A61K 45/00; A61K 2039/505; C12N 2310/14; C12N 15/1138; C07K 16/28; C07K 2317/76
See application file for complete search history.

(56) References Cited

U.S. PATENT DOCUMENTS

2003/0215884 A1 11/2003 Hunt
2012/0202705 A1 8/2012 Oberbauer et al.
2016/0202269 A1 7/2016 Yamashita et al.

FOREIGN PATENT DOCUMENTS

WO WO 2015/025770 A1 2/2015

OTHER PUBLICATIONS

Yamada et al. Increased Expression of Fibronectin Leucine-Rich Transmembrane Protein 3 in the Dorsal Root Ganglion Induces Neuropathic Pain in Rats. Journal of Neuroscience Sep. 18, 2019, 39 (38) 7615-7627.*
Lu et al. Structural Basis of Latrophilin—FLRT—UNC5 Interaction in Cell Adhesion. Structure. Sep. 1, 2015; 23(9): 1678-1691. Published online Jul. 30, 2015. doi: 10.1016/j.str.2015.06.024.*
Cai, Yan et al., "Prokaryotic expression and purification of fibronectin leucine rich transmembrane protein 3 C-terminal domain proteins in rats" Neural Regeneration Research, Feb. 2009, pp. 152-156, vol. 4, Issue 2.
Chen, Xuejun et al., "A Protocadherin-Cadherin-FLRT3 Complex Controls Cell Adhesion and Morphogenesis" PLoS ONE, Dec. 2009, pp. 1-9, vol. 4, Issue 12, e8411.
Dworkin, Robert H. et al., "Pharmacologic management of neuropathic pain: Evidence-based recommendations" PAIN, 2007, pp. 237-251, vol. 132.
Hayano, Yasufumi et al., "Netrin acts as a pain-inducing factor in the adult spinal cord" Pain Research, Jun. 2014, p. 96, vol. 29, No. 2, A3-1.
Lacy, Susan E. et al. "Identification of FLRT1, FLRT2, and FLRT3: A Novel Family of Transmembrane Leucine-Rich Repeat Proteins" Genomics, 1999, pp. 417-426, vol. 62.
Markman, John D. et al., "Ion Channel Targets and Treatment Efficacy in Neuropathic Pain" The Journal of Pain, Jan. 2006, pp. S38-S47, Supplement 1, vol. 7, No. 15.
Robinson, M. et al., "FLRT3 is expressed in sensory neurons after peripheral nerve injury and regulates neurite outgrowth" Molecular and Cellular Neuroscience, 2004, pp. 202-214, vol. 27.
Seiradake, Elena et al., "FLRT Structure: Balancing Repulsion and Cell Adhesion in Cortical and Vascular Development" Neuron, Oct. 2014, pp. 370-385, vol. 84.
Tsuji, Lyuji et al., "FLRT3, a cell surface molecule containing LRR repeats and a FNIII domain, promotes neurite outgrowth" Biochemical and Biophysical Research Communications, 2004, pp. 1086-1091, vol. 313.

(Continued)

*Primary Examiner* — Gregory S Emch
(74) *Attorney, Agent, or Firm* — Knobbe, Martens, Olson & Bear, LLP (57) ABSTRACT

The present invention provides a screening method for a pain suppressor, which method comprises using FLRT3 to select a substance capable of inhibiting FLRT3 expression or a substance capable of inhibiting FLRT3 transport to the spinal cord. In addition, the present invention provides a pharmaceutical composition for prevention or treatment of pain, which pharmaceutical composition comprises, as an active ingredient, a substance capable of inhibiting FLRT3 expression or a substance capable of inhibiting FLRT3 transport to the spinal cord.

7 Claims, 3 Drawing Sheets

Specification includes a Sequence Listing.

(56) References Cited

OTHER PUBLICATIONS

Woolf, Clifford J. et al., "Neuronal Plasticity: Increasing the Gain in Pain" Science, Jun. 2000, pp. 1765-1768, vol. 288.
Yamada, Moe et al., "Shinkei Shogaisei Totsu ni Okeru Sekizui FLRT3 Bunshi no Kino Kaiseki", Annual Meeting of the Japanese Biochemical Society(Web), Nov. 2015, p. 4TTOKUP-11(3P1244), vol. 88.
Yamagishi, Satoru "Kagayake Jidai no Ninaitetachi Dainohishitu Hassei ni Okeru Maku Kantsugata Tanpakushitsu FLRT2 no Hanpatsusei Guidance Inshi toshiteno Yakuwari" Bulletin of the Japanese Society for Neurochemistry, 2014, pp. 13-22, vol. 53, No. 1.
Yamagishi, Satoru "FLRT family proteins act as repulsive guidance cues for Unc5-positive neurons" Journal of Japanese Biochemical Society, 2014, pp. 493-497, vol. 86, No. 4.
Yamagishi, Satoru et al., "FLRT2 and FLRT3 act as repulsive guidance cues for Unc5-positive neurons" The EMBO Journal, 2011, pp. 1-14.
International Search Report for PCT/JP2016/053919 dated Apr. 26, 2016.
Written Opinion of the International Searching Authority for PCT/JP2016/053919 dated Apr. 26, 2016.
Hayano et al. (2016) Dorsal horn interneuron-derived Netrin-4 contributes to spinal sensitization in chronic pain via Unc5B. The Journal of Experimental Medicine. 213(13):2949-2966.
Leinders et al. (2014) Differential distribution of P13K isoforms in spinal cord and dorsal root ganglia: Potential roles in acute inflammatory pain. PAIN. 155(6):1150-1160.
Extended European Search Report for Application No. PCT/JP2016053919 dated Oct. 8, 2018.

\* cited by examiner

**Dorsal root ganglia
at Day 7 post-injury**

Fig. 4

**Spinal cord at
Day 7 post-injury**

SEQUENCE LISTING

<160> NUMBER OF SEQ ID NOS: 3

<210> SEQ ID NO 1
<211> LENGTH: 2061
<212> TYPE: DNA
<213> ORGANISM: Homo sapiens

<400> SEQUENCE: 1

| | | | | | |
|---|---|---|---|---|---|
| ttctgaagta | acggaagcta | ccttgtataa | agacctcaac | actgctgacc | atgatcagcg | 60 |
| cagcctggag | catcttcctc | atcgggacta | aaattgggct | gttccttcaa | gtagcacctc | 120 |
| tatcagttat | ggctaaatcc | tgtccatctg | tgtgtcgctg | cgatgcgggt | ttcatttact | 180 |
| gtaatgatcg | cttctgaca | tccattccaa | caggaatacc | agaggatgct | acaactctct | 240 |
| accttcagaa | caaccaaata | aataatgctg | ggattccttc | agatttgaaa | aacttgctga | 300 |
| aagtagaaag | aatataccta | taccacaaca | gtttagatga | atttcctacc | aacctcccaa | 360 |
| agtatgtaaa | agagttacat | ttgcaagaaa | ataacataag | gactatcact | tatgattcac | 420 |
| tttcaaaaat | tccctatctg | gaagaattac | atttagatga | caactctgtc | tctgcagtta | 480 |
| gcatagaaga | gggagcattc | cgagacagca | actatctccg | actgctttc | ctgtcccgta | 540 |
| atcaccttag | cacaattccc | tggggtttgc | ccaggactat | agaagaacta | cgcttggatg | 600 |
| ataatcgcat | atccactatt | tcatcaccat | ctcttcaagg | tctcactagt | ctaaaacgcc | 660 |
| tggttctaga | tggaaacctg | ttgaacaatc | atggtttagg | tgacaaagtt | ttcttcaacc | 720 |
| tagttaattt | gacagagctg | tccctggtgc | ggaattccct | gactgctgca | ccagtaaacc | 780 |
| ttccaggcac | aaacctgagg | aagctttatc | ttcaagataa | ccacatcaat | cgggtgcccc | 840 |
| caaatgcttt | ttcttatcta | aggcagctct | atcgactgga | tatgtccaat | aataacctaa | 900 |
| gtaatttacc | tcagggtatc | tttgatgatt | tggacaatat | aacacaactg | attcttcgca | 960 |
| acaatccctg | gtattgcggg | tgcaagatga | aatgggtacg | tgactggtta | caatcactac | 1020 |
| ctgtgaaggt | caacgtgcgt | gggctcatgt | gccaagcccc | agaaaaggtt | cgtgggatgg | 1080 |
| ctattaagga | tctcaatgca | gaactgtttg | attgtaagga | cagtgggatt | gtaagcacca | 1140 |
| ttcagataac | cactgcaata | cccaacacag | tgtatcctgc | ccaaggacag | tggccagctc | 1200 |
| cagtgaccaa | acagccagat | attaagaacc | ccaagctcac | taaggatcaa | caaaccacag | 1260 |
| ggagtccctc | aagaaaaaca | attacaatta | ctgtgaagtc | tgtcacctct | gataccattc | 1320 |
| atatctcttg | gaaacttgct | ctacctatga | ctgctttgag | actcagctgg | cttaaactgg | 1380 |
| gccatagccc | ggcatttgga | tctataacag | aaacaattgt | aacagggaa | cgcagtgagt | 1440 |
| acttggtcac | agccctggag | cctgattcac | cctataaagt | atgcatggtt | cccatggaaa | 1500 |
| ccagcaacct | ctacctattt | gatgaaactc | ctgtttgtat | tgagactgaa | actgcacccc | 1560 |
| ttcgaatgta | caaccctaca | accaccctca | atcgagagca | agagaaagaa | ccttacaaaa | 1620 |
| accccaattt | acctttggct | gccatcattg | gtggggctgt | ggccctggtt | accattgccc | 1680 |
| ttcttgcttt | agtgtgttgg | tatgttcata | ggaatggatc | gctcttctca | aggaactgtg | 1740 |
| catatagcaa | agggaggaga | agaaaggatg | actatgcaga | agctggcact | aagaaggaca | 1800 |
| actctatcct | ggaaatcagg | gaaacttctt | ttcagatgtt | accaataagc | aatgaaccca | 1860 |
| tctcgaagga | ggagtttgta | atacacacca | tatttcctcc | taatgaatg | aatctgtaca | 1920 |
| aaaacaatca | cagtgaaagc | agtagtaacc | gaagctacag | agacagtggt | attccagact | 1980 |
| cagatcactc | acactcatga | tgctgaagga | ctcacagcag | acttgtgttt | tgggttttt | 2040 |
| aaacctaagg | gaggtgatgg | t | | | | 2061 |

```
<210> SEQ ID NO 2
<211> LENGTH: 21
<212> TYPE: DNA
<213> ORGANISM: Homo sapiens

<400> SEQUENCE: 2
ctgctgacca tgatcagcgc a                                              21

<210> SEQ ID NO 3
<211> LENGTH: 21
<212> TYPE: DNA
<213> ORGANISM: Artificial Sequence
<220> FEATURE:
<223> OTHER INFORMATION: anti-sense oligonucleotide

<400> SEQUENCE: 3
tgggctgatc atggtcagca g                                              21
```

SCREENING METHOD FOR PAIN SUPPRESSOR AND PHARMACEUTICAL COMPOSITION FOR PREVENTION OR TREATMENT OF PAIN

CROSS REFERENCE TO RELATED APPLICATIONS

This application claims priority to and is a divisional application of U.S. patent application Ser. No. 15/542,859, filed on Jul. 11, 2017, which is a U.S. National Phase Application of PCT International Application Number PCT/JP2016/053919, filed on Feb. 10, 2016, designating the United States of America and published in the Japanese language, which is an International Application of and claims the benefit of priority to Japanese Patent Application No. 2015-025954, filed on Feb. 13, 2015. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 37 U.S.C. § 1.52(e). The name of the ASCII text file for the Sequence Listing is SeqList-IWAT007-001D1.txt, the date of creation of the ASCII text file is Feb. 26, 2020, and the size of the ASCII text file is 4 KB.

TECHNICAL FIELD

The present invention relates to a screening method for a pain suppressor. The present invention also relates to a pharmaceutical composition for treatment or prevention of pain.

BACKGROUND ART

Pain is an intractable disease which reduces the QOL (Quality of Life) of the affected individuals. The number of chronic pain sufferers in the world is reported to exceed 20 million, and the combined market size of Japan, the U.S. and Europe for pain medicines is said to be about 2 trillion yen. In addition, the number of patients with diseases which may be a cause of pain, such as stroke, cancer, diabetes and viral infection, has been increasing, and under such circumstances, the establishment of an appropriate treatment modality for pain is a very important medical issue. Particularly, neuropathic pain is less sensitive to nonsteroidal antiinflammatory drugs and opioid analgesics, and is a disease with significant unmet medical needs. However, the pathogenesis of neuropathic pain is diverse and the underlying molecular mechanism is very complicated. Therefore, radical therapeutic medicines for neuropathic pain are yet to be developed (Non Patent Literature 1). Clarifying the molecular mechanism of the development and maintenance of neuropathic pain leads to the development of breakthrough medicines and is expected to provide a promising solution to one of the biggest medical issues in the 21st century.

The dorsal horn of the spinal cord is considered to be one of the major causative site of neuropathic pain (Non Patent Literature 2). Peripheral sensory inputs undergo various processing, such as amplification, attenuation and integration, in the dorsal horn of the spinal cord, and are transmitted to the brain. However, injury of peripheral nerves reportedly induces neural network changes in the dorsal horn of the spinal cord, for example abnormal axon collateral formation and enhanced synaptic transmission, thus triggering pain (Non Patent Literature 3). Therefore, clarifying a novel molecular mechanism which regulates the neural circuit in the dorsal horn of the spinal cord is expected to lead to the discovery of a novel target molecule required for the development of breakthrough medicines for pain.

FLRT3 (fibronectin and leucine-rich transmembrane protein-3) is a member of the fibronectin leucine-rich repeat transmembrane protein family and has a FN (fibronectin) type III domain and leucine-rich repeats. FLRT3 is expressed in various tissues including kidney, skeletal muscle, brain and lung (Non Patent Literature 4). FLRT3 is reported to play important roles in the cell and tissue morphogenesis during early embryogenesis, including neurite formation (Non Patent Literature 5), cell adhesion (Non Patent Literature 6), axon guidance (Non Patent Literature 7), etc. Also reported is that, after peripheral nerve injury, FLRT3 protein expression increases at the axon terminals of dorsal root ganglion neurons projecting into the dorsal horn of the spinal cord (Non Patent Literature 8). Moreover, FLRT3 is reported to bind to the Unc5B receptor (Non Patent Literature 7 and 9). However, there have been no study reports on the in vivo functions of FLRT3 in the adult spinal cord, and it has yet to be clarified whether FLRT3 is involved in the development of neuropathic pain.

CITATION LIST

Non Patent Literature

Non Patent Literature 1:
Dworkin, R. H. et al. Pharmacologic management of neuropathic pain: evidence-based recommendations. Pain 132, 237-51 (2007).
Non Patent Literature 2:
Woolf, C. J. Neuronal Plasticity: Increasing the Gain in Pain. Science 288, 1765-1768 (2000).
Non Patent Literature 3:
Markman J. D. & Dworkin, R. H. Ion channel targets and treatment efficacy in neuropathic pain. The journal of pain 7, S38-47 (2006).
Non Patent Literature 4:
Lacy, S. E., Bo, C. G., Buzney, E. A., Kunkel, L. M. & Al, L. E. T. Identification of FLRT1, FLRT2, and FLRT3: A Novel Family of Transmembrane Leucine-Rich Repeat Proteins. 426, 417-426 (1999).
Non Patent Literature 5:
Tsuji, L. et al. FLRT3, a cell surface molecule containing LRR repeats and a FNIII domain, promotes neurite outgrowth. Biochemical and Biophysical Research Communications 313, 1086-1091 (2004).
Non Patent Literature 6:
Chen, X., Koh, E., Yoder, M. & Gumbiner, B. M. A protocadherin-cadherin-FLRT3 complex controls cell adhesion and morphogenesis. PloS one 4, e8411 (2009).
Non Patent Literature 7:
Yamagishi, S. et al. FLRT2 and FLRT3 act as repulsive guidance cues for Unc5-positive neurons. 1-14 (2011). doi: 10.1038/emboj.2011.189
Non Patent Literature 8:
Robinson, M. et al. FLRT3 is expressed in sensory neurons after peripheral nerve injury and regulates neurite outgrowth. Molecular and cellular neurosciences 27, 202-14 (2004).

Non Patent Literature 9:
Seiradake E. et al. FLRT structure: balancing repulsion and cell adhesion in cortical and vascular development. Neuron, 84(2), 370-385 (2014).

SUMMARY OF INVENTION

Technical Problem

An object of the present invention is to find a molecule involved in peripheral neuropathy-associated pain and to provide a screening method for a pain suppressor. Another object of the present invention is to provide a pharmaceutical composition for prevention or treatment of pain, which composition comprises a novel active ingredient.

Solution to Problem

The present invention includes the following to achieve the above-mentioned objects.
(1) A screening method for a pain suppressor, the method comprising using FLRT3.
(2) The method according to the above (1), wherein the pain suppressor is a substance capable of suppressing peripheral neuropathy-associated pain.
(3) The method according to the above (1) or (2), wherein a substance capable of inhibiting FLRT3 expression is selected.
(4) The method according to the above (1) or (2), wherein a substance capable of inhibiting FLRT3 transport to spinal cord is selected.
(5) The method according to the above (1) or (2), wherein a substance capable of inhibiting FLRT3 binding to Unc5B is selected.
(6) The method according to the above (3), comprising the steps of:
  bringing a test substance into contact with cells expressing FLRT3;
  measuring the level of FLRT3 expression in the cells; and
  comparing the level of FLRT3 expression to that in FLRT3-expressing cells not in contact with the test substance to determine whether or not the test substance is capable of reducing the level of FLRT3 expression.
(7) The method according to the above (4), comprising the steps of:
  bringing a test substance into contact with dorsal root ganglion cells in dorsal root ganglion tissue;
  measuring the level of FLRT3 in dorsal root fibers or spinal cord; and
  comparing the level of FLRT3 to that in dorsal root fibers or spinal cord in the absence of contact with the test substance to determine whether or not the test substance is capable of reducing the level of FLRT3.
(8) The method according to the above (5), comprising the steps of:
  bringing a test substance into contact with FLRT3 and Unc5B;
  assessing FLRT3 binding to Unc5B; and
  determining whether or not the test substance is capable of inhibiting FLRT3 binding to Unc5B.
(9) A pharmaceutical composition for prevention or treatment of pain, comprising, as an active ingredient, a substance capable of inhibiting FLRT3 expression, a substance capable of inhibiting FLRT3 transport to spinal cord, or a substance capable of inhibiting FLRT3 binding to Unc5B.
(10) The pharmaceutical composition according to the above (9), wherein the pain is peripheral neuropathy-associated pain.
(11) The pharmaceutical composition according to the above (9) or (10), wherein the substance capable of inhibiting FLRT3 expression is a nucleic acid capable of inhibiting FLRT3 expression.
(12) The pharmaceutical composition according to the above (9) or (10), wherein the substance capable of inhibiting FLRT3 transport to spinal cord or the substance capable of inhibiting FLRT3 binding to Unc5B is an antibody or a peptide capable of specifically binding to FLRT3.
(13) The pharmaceutical composition according to anyone of the above (9) to (12), wherein the pharmaceutical composition has an action at dorsal root ganglion cells, dorsal root fibers or axon terminals of dorsal root ganglion neurons.

Advantageous Effects of Invention

The screening method of the present invention enables the discovery of a pain suppressor useful as a preventive or therapeutic medicine for pain. In addition, the pharmaceutical composition of the present invention is useful for prevention or treatment of pain.

DESCRIPTION OF EMBODIMENTS

Screening Method

The present invention provides a screening method for a pain suppressor. The screening method of the present invention comprises using FLRT3. The FLRT3 used in the screening method of the present invention may be a protein or a gene. In the case where the FLRT3 is a protein, the protein may be a full-length one or a functional fragment thereof.

The FLRT3 used in the screening method of the present invention may be of any living organism and is not particularly limited. Preferred is a mammalian FLRT3. The mammal is preferably a human, a chimpanzee, a monkey, a dog, a cow, a mouse, a rat, a guinea pig or the like, and is more preferably a human. Information regarding the nucleotide sequences of the genes encoding FLRT3 proteins of various animals and the amino acid sequences of the FLRT3 proteins can be obtained from known databases (e.g., DDBJ/GenBank/EMBL) with the respective accession numbers shown in Table 1, for example.

TABLE 1

|  | Nucleotide sequence | Amino acid sequence |
|---|---|---|
| Human | AY358319 | AAQ88685 |
| Rat | NM_001126291 | AAI60843 |
| Mouse | NM_001172160 | AAH52043 |

The test substances to be screened are preferably nucleic acids, peptides, proteins, non-peptidic compounds, synthetic compounds, fermentation products, cell extracts, cell culture supernatants, plant extracts, mammalian tissue extracts and plasma, etc., but are not limited to these examples. The test substances may be novel or known substances. These test substances may be in the form of a salt. The salt is composed of the test substance with a physiologically acceptable acid or base.

In the screening method of the present invention, it is preferred to select a substance capable of inhibiting FLRT3 expression or a substance capable of inhibiting FLRT3 transport to the spinal cord. The present inventors have found that a rat partial sciatic nerve ligation model shows a significant increase in FLRT3 gene and protein expression in dorsal root ganglion cells on the side ipsilateral to the injury, followed by the transport of the expressed FLRT3 protein to the spinal cord through dorsal root fibers (axons), resulting in pain amplification (see Examples). Therefore, a substance capable of inhibiting FLRT3 expression in dorsal root ganglion cells and a substance capable of inhibiting FLRT3 protein transport from dorsal root ganglion cells to the spinal cord are expected to be capable of suppressing peripheral neuropathy-associated pain.

In the screening method of the present invention, it is also preferred to select a substance capable of inhibiting FLRT3 binding to Unc5B. Since FLRT3 is reported to bind to the Unc5B receptor (Non Patent Literature 7 and 9), a substance capable of inhibiting FLRT3 binding to Unc5B is expected to be capable of inhibiting the downstream signaling from FLRT3 and thus suppressing peripheral neuropathy-associated pain.

For the selection of the substance capable of inhibiting FLRT3 expression in the screening method of the present invention, the screening method can comprise, for example, the following steps:

bringing a test substance into contact with cells expressing FLRT3;
measuring the level of FLRT3 expression in the cells; and
comparing the level of FLRT3 expression to that in FLRT3-expressing cells not in contact with the test substance to determine whether or not the test substance is capable of reducing the level of FLRT3 expression.

The cells expressing FLRT3 may be cells in the living body or cultured cells. The cultured cells may be primary cultured cells or a cell line. Examples of the primary cultured cells include dorsal root ganglion cells, rostral thalamic nucleus cells, hippocampal dentate granule cells, human umbilical artery endothelial cells (HUAEC), and examples of the cell line include Hela cells. In addition, a FLRT3-expressing transformant with a recombinant expression vector containing a DNA encoding FLRT3 can be used.

The method for bringing the test substance into contact with the cells is not particularly limited and may be any method that allows the contact of the test substance with the cells. For example, in the case where cultured cells are used, the contact can be achieved by, for example, addition of the test substance to culture medium. In the case where the test substance is brought into contact with cells in the living body, the contact can be achieved by systemic administration such as oral, intravenous or intraperitoneal administration, local administration to a target organ or tissue, or the like. In addition, it is preferable to prepare a control group not in contact with the test substance.

In the measurement of the level of FLRT3 expression, the level of FLRT3 expression may be the protein level of FLRT3 or the mRNA level of FLRT3. The measurement of the FLRT3 protein level can be achieved by extracting proteins from the cells by a known method and quantifying FLRT3 protein by a known method for protein measurement. Examples of the known method for protein measurement include western blotting, EIA, ELISA, RIA and a method using a protein assay reagent. The measurement of the FLRT3 mRNA level can be achieved by extracting RNAs by a known method and quantifying FLRT3 mRNA by a known method for mRNA measurement. Examples of the known method for mRNA measurement include northern blotting, RT-PCR, quantitative RT-PCR and RNase protection assay.

When the protein or mRNA level of FLRT3 after the contact with the test substance is reduced as compared with that in the control group (not in contact with the test substance), the test substance can be determined as the desired substance. The selection criterion for the reduction of the protein or mRNA level of FLRT3 is not particularly limited. For example, when the test substance reduces the protein or mRNA level of FLRT3 to preferably 50% or less, more preferably 25% or less of that in the cells not in contact with the test substance, the test substance can be determined as the desired substance.

For the selection of the substance capable of inhibiting FLRT3 transport to the spinal cord in the screening method of the present invention, the screening method can comprise, for example, the following steps:

bringing a test substance into contact with dorsal root ganglion cells in dorsal root ganglion tissue;
measuring the level of FLRT3 in dorsal root fibers or spinal cord; and
comparing the level of FLRT3 to that in dorsal root fibers or spinal cord in the absence of contact with the test substance to determine whether or not the test substance is capable of reducing the level of FLRT3.

The screening method may be performed in vivo or in vitro.

In the case where the screening method is performed in vivo, it is preferred to use neuropathic pain model animals (e.g., a partial sciatic nerve ligation model (see Examples) etc.). The contact of the test substance with the dorsal root ganglion cells in the dorsal root ganglion tissue can be achieved by systemic administration such as oral, intravenous or intraperitoneal administration, local administration to a target tissue, or the like. In addition, it is preferable to prepare a control group not in contact with the test substance. After the contact, the dorsal root fibers or the spinal cord is harvested, proteins are extracted from the harvested tissue by a known method, and FLRT3 is quantified by a known method for protein measurement. Examples of the known method for protein measurement include western blotting, EIA, ELISA, RIA and a method using a protein assay reagent.

In the case where the screening method is performed in vitro, for example, dorsal root ganglion tissue is harvested from an experimental animal such as a rat and cultured in a commercial compartment chamber for neuronal cells (manufactured by Tyler Research Corporation) to prepare an experimental system which allows separate treatment of dorsal root ganglion cell bodies and dorsal root fibers (axons) with the test substance (References: Melli G, Keswani S C, Fischer A, Chen W, Hoke A. Spatially distinct and functionally independent mechanisms of axonal degeneration in a model of HIV-associated sensory neuropathy. Brain. 2006 May; 129(Pt 5): 1330-8. Epub 2006 Mar. 14., and Pazyra-Murphy M F, Segal R A. Preparation and maintenance of dorsal root ganglia neurons in compartmented cultures. J Vis Exp. 2008 Oct. 17; (20). pii: 951. doi: 10.3791/951). For the contact of the test substance with the dorsal root ganglion cells, the test substance is added to culture medium only in the cell body compartment or in both the compartments. After that, the dorsal root fibers (axons) are harvested, proteins are extracted from the harvested tissue by a known method, and FLRT3 is quantified by a known method for protein measurement. Examples of the medium used for the culture of the dorsal root ganglion tissue include Ham's F-12 medium with 2% B-27 Supplement (trade name, Life Technologies). The culture of the dorsal root ganglion tissue can be performed by a known culture method (for example, Kim S U, Tomonaga M, Ghetti B. Neurofibrillary degeneration in cultured adult mouse neurons induced by maytansine. Acta Neuropathol. 1980; 52(2): 161-4., or Yong V W, Horie H, Kim S U. Comparison of six different substrata on the plating efficiency, differentiation and survival of human dorsal root ganglion neurons in culture. Dev Neurosci. 1988; 10(4): 222-30) or a modified method thereof.

When the level of FLRT3 in the dorsal root fibers or the spinal cord after the contact with the test substance is reduced as compared with that in the control group (not in contact with the test substance), the test substance can be determined as the desired substance. The selection criterion for the reduction of the level of FLRT3 in the dorsal root fibers or the spinal cord is not particularly limited. For example, when the test substance reduces the level of FLRT3 to preferably 50% or less, more preferably 25% or less of that in the control group, the test substance can be determined as the desired substance.

For the selection of the substance capable of inhibiting FLRT3 binding to Unc5B in the screening method of the present invention, the screening method can comprise, for example, the following steps:

bringing a test substance into contact with FLRT3 and Unc5B;

assessing FLRT3 binding to Unc5B; and determining whether or not the test substance is capable of inhibiting FLRT3 binding to Unc5B.

The FLRT3 and the Unc5B used may be native or recombinant proteins. In the case where the FLRT3 and the Unc5B used are native proteins, the native proteins can be obtained by a known method (for example, affinity column method) from the culture supernatant or cell extract of cells expressing FLRT3 and/or Unc5B. In the case where the FLRT3 and the Unc5B used are recombinant proteins, the recombinant proteins can be obtained by a known method from the culture supernatant or cell extract of cells transfected with a FLRT3 expression vector or a Unc5B expression vector. The recombinant FLRT3 protein can be produced by known recombinant techniques with the use of genetic information obtainable from known databases (e.g., DDBJ/GenBank/EMBL) (see Table 1). Information regarding the nucleotide sequences of the genes encoding Unc5B proteins of various animals and the amino acid sequences of the Unc5B proteins can be obtained from known databases (e.g., DDBJ/GenBank/EMBL) with the respective accession numbers shown in Table 2, for example. The recombinant Unc5B protein can be produced by known recombinant techniques with the use of such genetic information.

TABLE 2

|  | Nucleotide sequence | Amino acid sequence |
| --- | --- | --- |
| Human | NM_170744 | NP_734465 |
| Monkey | XM_001106162 | XP_001106162 |
| Mouse | NM_029770 | NP_084046 |
| Rat | NM_022207 | NP_071543 |
| Guinea pig | XM_003473767 | XP_003473815 |

The method for bringing the test substance into contact with FLRT3 and Unc5B is not particularly limited. For example, a reaction system containing FLRT3 and Unc5B is prepared, and the test substance is added thereto. The contact time and temperature are not particularly limited and can be selected as appropriate. In addition, it is preferable to prepare a control group not in contact with the test substance.

The method for assessing FLRT3 binding to Unc5B is not particularly limited, and a known method for determining the level of FLRT3 binding to Unc5B can be selected as appropriate. For example, ELISA, fluorescence polarization, etc. can preferably be used. In an exemplary method using ELISA, either FLRT3 or Unc5B is immobilized, the other one and the test substance are added thereto so that the reaction proceeds, and the level of FLRT3 binding to Unc5B is determined with the use of appropriate primary and secondary antibodies.

The method for determining whether or not the test substance is capable of inhibiting FLRT3 binding to Unc5B is not particularly limited. When the level of FLRT3 binding to Unc5B after the contact with the test substance is reduced as compared with that in the control group (not in contact with the test substance), the test substance can be determined as the desired substance. The selection criterion for the reduction of the level of FLRT3 binding to Unc5B is not particularly limited. For example, when the test substance reduces the level of FLRT3 binding to Unc5B to preferably 50% or less, more preferably 25% or less of that in the absence of contact with the test substance, the test substance can be determined as the desired substance.

Pharmaceutical Composition for Prevention or Treatment of Pain

The present invention provides a pharmaceutical composition for prevention or treatment of pain, the pharmaceutical composition comprising, as an active ingredient, a substance capable of inhibiting FLRT3 expression, a substance capable of inhibiting FLRT3 transport to the spinal cord, or a substance capable of inhibiting FLRT3 binding to Unc5B. The pharmaceutical composition of the present invention preferably comprises, as an active ingredient, a substance selected using the above-described screening method of the present invention. The pharmaceutical composition of the present invention is suitable for the prevention or treatment of peripheral neuropathy-associated pain.

The pharmaceutical composition of the present invention can be prepared in the usual manner in a dosage form containing, as an active ingredient, the substance capable of inhibiting FLRT3 expression, the substance capable of inhibiting FLRT3 transport to the spinal cord, or the substance capable of inhibiting FLRT3 binding to Unc5B. For example, the dosage form can be an oral preparation and the examples include solid or liquid preparations, specifically tablets (including sugar-coated tablets and film-coated tablets), pills, granules, powders, capsules (including soft capsules), syrups, emulsions, suspensions, etc. These preparations can be produced by known methods and contain one or more carriers, diluents or excipients commonly used in the field of pharmaceutical formulation. For example, carriers or excipients used for tablets include lactose, starch, sucrose and magnesium stearate. The dosage form may be a parenteral preparation and the examples include injections and suppositories. The injections include an intravenous injection, a subcutaneous injection, an intracutaneous injection, an intramuscular injection, an intravenous infusion and an intraarticular injection. These injections are prepared according to known methods, for example, by dissolving, suspending or emulsifying the active ingredient in a sterile aqueous or oily liquid commonly used for injections. As an aqueous liquid for injection, for example, physiological saline, an isotonic solution containing glucose and an auxiliary substance, or the like can be used, optionally together with a suitable solubilizer such as alcohols (e.g., ethanol etc.), polyalcohols (e.g., propylene glycol, polyethylene glycol, etc.) and nonionic surfactants (e.g., polysorbate 80, HCO-50, etc.). As an oily liquid, for example, sesame oil, soybean oil or the like can be used, optionally together with a solubilizer such as benzyl benzoate and benzyl alcohol. Suppositories for rectal administration are prepared by mixing the active ingredient with a commonly used base for suppositories. The pharmaceutical preparations that can be obtained in the above manner are safe and less toxic, and therefore can be administered orally or parenterally to, for example, humans and other mammals (e.g., rats, mice, rabbits, sheep, pigs, cows, cats, dogs, monkeys, etc.).

The active ingredient of the pharmaceutical composition of the present invention is preferably a nucleic acid capable of inhibiting FLRT3 expression. Examples of the nucleic acid capable of inhibiting FLRT3 expression include a siRNA (short interfering RNA), a shRNA (short hairpin RNA) or an antisense oligonucleotide against FLRT3 gene. Information regarding the nucleotide sequence of the FLRT3 gene of an animal to be subjected to administration of the nucleic acid can easily be obtained from known databases (e.g., DDBJ/GenBank/EMBL). siRNA is a double-stranded RNA of about 20 bases (for example, about 21 to 23 bases) or less in length, and after expressed in cells, can inhibit the expression of its target gene (FLRT3 gene in the present invention). shRNA is a single-stranded RNA molecule having a partial palindromic sequence, and due to complementary base pairing within the palindromic sequence, forms an intramolecular short hairpin structure of about 20 base pairs or more with a 3'-terminal overhang. After introduced into cells, shRNA is intracellularly degraded to a form of about 20 bases in length (typically for example, 21, 22 or 23 bases) and can inhibit the expression of its target gene (FLRT3 gene in the present invention) as with siRNA. The siRNA and the shRNA may be in any form that can inhibit FLRT3 expression. The siRNA and the shRNA can be designed based on the nucleotide sequence of the target gene by a known method. The siRNA and the shRNA can be artificially produced by chemical synthesis. Alternatively, for example, T7 RNA polymerase and T7 promoter may be used for in vitro production of antisense or sense RNA from a template DNA. The antisense oligonucleotide is a nucleotide that is complementary or hybridizable to a contiguous 5 to 100 bases in the DNA sequence of FLRT3 gene, and may be DNA or RNA. The antisense oligonucleotide may be modified unless its function is compromised by such modification. The antisense oligonucleotide can be produced in the usual manner, and for example, can easily be produced with a commercial DNA synthesizer.

In the case where the active ingredient of the pharmaceutical composition of the present invention is a nucleic acid capable of inhibiting FLRT3 expression, it can be administered in the form of a non-viral or viral vector. In the case of administration in the form of a non-viral vector, a method using liposomes to introduce nucleic acid molecules (the liposome method, the HVJ-liposome method, the cationic liposome method, the lipofection method, the lipofectamine method, etc.), microinjection, a method using a gene gun to introduce nucleic acid molecules and a carrier (metal particles), and other methods can be used. In the case where a viral vector is used for siRNA or shRNA administration to the living body, viral vectors such as recombinant adenoviruses and retroviruses can be used. A DNA encoding the siRNA or the shRNA of interest is introduced into a nontoxic DNA or RNA virus such as nontoxic strains of retrovirus, adenovirus, adeno-associated virus, herpesvirus, vaccinia virus, poxvirus, poliovirus, Sindbis virus, Sendai virus or SV40, and the resulting recombinant virus is allowed to infect cells or tissues for introduction of the gene of interest into the cells or tissues.

Robinson et al. have reported that the antisense oligonucleotide consisting of the nucleotide sequence represented by SEQ ID NO: 3 (TGGGCTGATCATGGTCAGCAG) suppresses the expression of rat FLRT3 (Robinson, M. et al. FLRT3 is expressed in sensory neurons after peripheral nerve injury and regulates neurite outgrowth. Molecular and cellular neurosciences 27, 202-14 (2004)). The target sequence of this rat antisense oligonucleotide corresponds to the segment from positions 42 to 62 of the nucleotide sequence of the human FLRT3 gene (SEQ ID NO: 1), the sequence of which segment is CTGCTGACCATGATCAGCGCA (SEQ ID NO: 2). Therefore, an antisense oligonucleotide targeting this segment is expected to be useful as an active ingredient of the pharmaceutical composition of the present invention.

The active ingredient of the pharmaceutical composition of the present invention is preferably a peptide or an antibody capable of specifically binding to FLRT3. The binding of the antibody or the peptide to FLRT3 can inhibit FLRT3 transport to the spinal cord. In addition, the binding of the antibody or the peptide to FLRT3 can inhibit FLRT3 binding to Unc5B. The antibody capable of specifically binding to FLRT3 may be a polyclonal or monoclonal antibody. The antibody may be a whole antibody molecule or an antibody fragment (for example, Fab, F(ab')$_2$, Fab', Fv, scFv, etc.) capable of specifically binding to an antigen of interest. The antibody is preferably a chimeric human antibody or a humanized antibody. The antibody and the peptide can be produced by known methods. In the case where the active ingredient of the pharmaceutical composition of the present invention is a peptide or an antibody, the pharmaceutical composition is preferably administered in the form of an injection or an infusion containing the active ingredient and a pharmaceutically acceptable carrier via a parenteral route, for example, intravenously, intramuscularly, intracutaneously, intraperitoneally, subcutaneously or locally.

The pharmaceutical composition of the present invention can comprise 0.001 to 50% by mass, preferably 0.01 to 10% by mass, and more preferably 0.1 to 1% by mass of the active ingredient.

The dose of the pharmaceutical composition of the present invention is appropriately determined in consideration of the purpose, the type and severity of the disease, the age, body weight, sex and medical history of the patient, the kind of the active ingredient, etc. In the case where the subject is an average human weighing about 65 to 70 kg, the daily dose is preferably about 0.02 to 4000 mg, and more preferably about 0.1 to 200 mg. The total daily dose may be given as a single dose or in divided doses.

The active ingredient of the pharmaceutical composition of the present invention preferably acts at dorsal root ganglion cells, dorsal root fibers or the axon terminals of dorsal root ganglion neurons, and more preferably acts at dorsal root ganglion cells or dorsal root fibers. In the case where the active ingredient of the pharmaceutical composition of the present invention is a substance capable of inhibiting FLRT3 expression or a substance capable of inhibiting FLRT3 transport to the spinal cord, the active ingredient acts, for example, at dorsal root ganglia to inhibit FLRT3 expression or at dorsal root fibers to inhibit FLRT3 transport from dorsal root ganglia to the spinal cord, resulting in the prevention or treatment of pain. Therefore, the active ingredient of the pharmaceutical composition of the present invention does not have to reach the central nervous system to exert the effects, and this is a great advantage. In the case where the active ingredient of the pharmaceutical composition of the present invention is a substance capable of inhibiting FLRT3 binding to Unc5B, it is preferred that the active ingredient acts at the axon terminals of dorsal root ganglion neurons because FLRT3 is considered to bind to Unc5B at the axon terminals of dorsal root ganglion neurons in the dorsal horn of the spinal cord.

The present invention further includes the following.
(A) A method for prevention or treatment of pain, comprising a step of administering an effective amount of a substance capable of inhibiting FLRT3 expression, a substance capable of inhibiting FLRT3 transport to the spinal cord, or a substance capable of inhibiting FLRT3 binding to Unc5B.
(B) A substance capable of inhibiting FLRT3 expression, a substance capable of inhibiting FLRT3 transport to the spinal cord, or a substance capable of inhibiting FLRT3 binding to Unc5B for use in the prevention or treatment of pain.
(C) Use of a substance capable of inhibiting FLRT3 expression, a substance capable of inhibiting FLRT3 transport to the spinal cord, or a substance capable of inhibiting FLRT3 binding to Unc5B for the production of a pharmaceutical composition for prevention or treatment of pain.

EXAMPLES

Hereinafter, the present invention will be illustrated in detail by examples, but the present invention is not limited thereto.

Example 1: Involvement of FLRT3 in Nociceptive Response 1-1 Experimental Methods
(1) Production of Neuropathic Pain Model A neuropathic pain model was produced by partial sciatic nerve ligation (Seltzer Z, A novel behavioral model of neuropathic pain disorders produced in rats by partial sciatic nerve injury. Pain 43, 205-18 (1990)) and used in the experiments described later. The specific procedure was as follows. Eight-week-old male Wistar/ST rats were anesthetized by inhalation of a gas mixture of isoflurane and oxygen, and the left hind thigh and groin of each rat was shaved. The shaved area was disinfected with alcohol. The skin and the muscle over the joint connecting the thigh bone to the hip bone were incised, and the sciatic nerve, which runs along with the thigh bone, was exposed. One-third to half of the sciatic nerve was ligated with a 4-0 nylon suture, and the muscle and skin incisions were sutured. In the contralateral (right) hind limb, the skin and the muscle were incised, but the sciatic nerve was left intact as a sham-operated control.

(2) Measurement of Pain-Related Behavior

The von Frey filament test was used to measure the response to mechanical stimulus. Prior to testing, the pain model rats were individually put into a plastic cage onto a wire mesh and acclimated to the environment for 5 to 10 minutes until settled. A filament (Semmes-Weinstein Von Frey Anesthesiometer, Muromachi Kikai Co., Ltd.) was applied to the center of the plantar surface of the hindpaw for 3 to 5 seconds, and the stimulus threshold for hindpaw withdrawal (g) was measured in an up-down method.

(3) Experiment of Intrathecal Administration of FLRT3 Protein

In 8-week-old male Wistar/ST rats, a polyethylene tube was inserted into the intrathecal space from the space between the 4th and 5th lumbar vertebrae and placed with the tip of the tube in the neighborhood of the lumbar enlargement (Milligan, E. D., Hinde, J. L., Mehmert, K. K., Maier, S. F. & Watkins, L. R. A method for increasing the viability of the external portion of lumbar catheters placed in the spinal subarachnoid space of rats. Journal of neuroscience methods 90, 81-6 (1999)). One week after the intubation, the von Frey filament test was performed to confirm whether or not the animals had intubation-caused motor or sensory dysfunction. The animals confirmed to have no intubation-caused motor or sensory dysfunction were used in the experiment shown below. A purified FLRT3 protein (R&D) was dissolved at a concentration of 40 ng/µL in physiological saline, and 10 µL of this solution was infused from the outer end of the indwelling intrathecal tube. Meanwhile, 10 µL of physiological saline was administered to control group animals. The von Frey filament test was performed at 12, 24 and 48 hours post-administration to examine the change in withdrawal threshold.

(4) Western Blotting

The spinal cord and the dorsal root ganglion cells of the neuropathic pain model rats were used as the samples. Each rat was anesthetized with excess somnopentyl, and blood was completely removed by perfusion with 100 mL of phosphate buffer. Lumbar vertebrae were cut, and right and left dorsal root ganglia at the 4th to 6th lumbar levels of the spinal cord were separately harvested. The dorsal root ganglia were lysed on ice with lysis buffer (50 mM Tris-HCl, 150 mM NaCl, 0.5% NP-40, 10 mM NaF, 1 mM $Na_3VO_4$) containing protease inhibitor cocktail (Roche). This crude lysate was centrifuged at 15,000 rpm at 4° C. for 10 minutes, and the supernatant was used as a cell lysate for the subsequent experiment. After the cell lysate was boiled in a sample buffer for 5 minutes, proteins in the cell lysate were separated by SDS-PAGE and transferred to a PVDF membrane. The membrane was blocked with 5% non-fat dry milk in PBS containing 0.05% Tween-20 (PBS-T) and incubated with an anti-FLRT3 antibody (Abcam) diluted in PBS-T at 4° C. overnight. After washing with PBS-T, the membrane was incubated with an HRP-labeled anti-rabbit IgG antibody (Cell Signaling Technology). The FLRT3 protein was detected using an ECL chemiluminescence system (GE Healthcare). The FLRT3 expression level was normalized to the beta-actin expression level.

(5) Quantitative PCR

The spinal cord and the dorsal root ganglion cells of the neuropathic pain model rats were used as the samples. Each rat was anesthetized with excess somnopentyl, and blood was completely removed by perfusion with 100 mL of phosphate buffer. Lumbar vertebrae were cut, and right and left dorsal root ganglia at the 4th to 6th lumbar levels of the spinal cord were separately harvested. RNA was extracted with a reagent (TRIZOL, Life Technologies) from the dorsal root ganglia, and cDNA was synthesized from the RNA with reverse transcriptase (High-capacity Reverse Transcription Kit, Life Technologies). The expression level of the rat FLRT3 gene was quantified with TaqMan probe (Life Technologies). The expression level of the rat FLRT3 gene was normalized to the expression level of the rat GAPDH gene (housekeeping gene).

1-2 Experimental Results (1) FLRT3 Gene Expression Level in Neuropathic Pain Model The FLRT3 gene expression under neuropathic pain conditions was analyzed by quantitative PCR. At 0, 4, 7, and 14 days after the production of the neuropathic pain model, spinal cord tissue (lumbar enlargement) and dorsal root ganglion cells on the side ipsilateral to the injury were separately harvested from each model rat. Similarly, the contralateral spinal cord tissue (lumbar enlargement) and dorsal root ganglion cells were also harvested. RNA extracted from each harvested sample was reverse transcribed into cDNA, and the expression of FLRT3 gene and GAPDH gene (reference) was analyzed by quantitative PCR.

Figure 1:
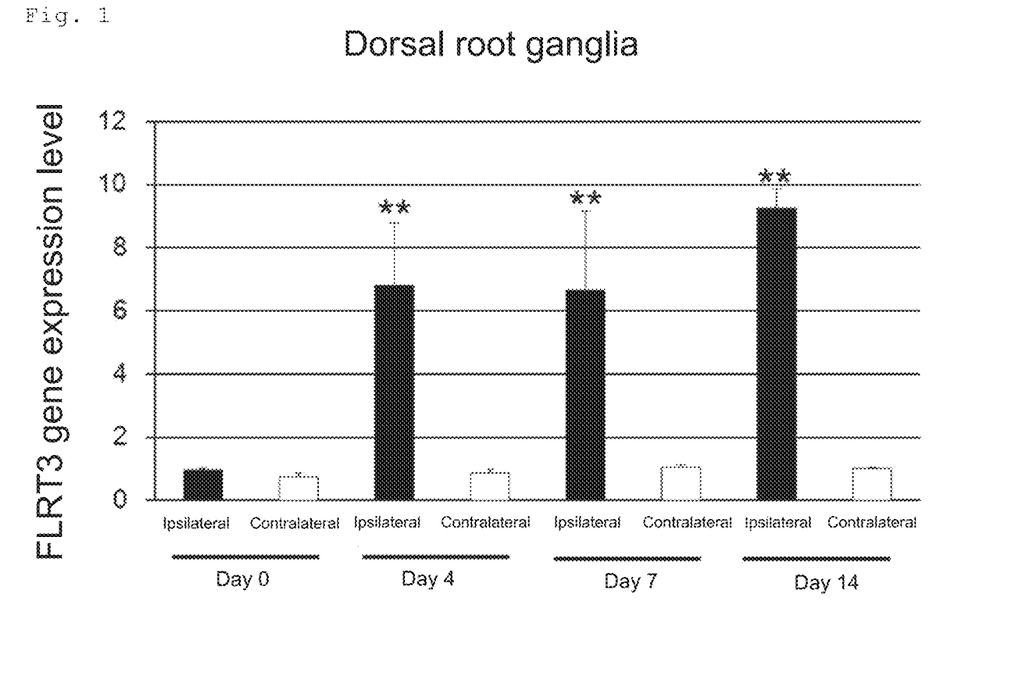
FIG. 1 shows the results of quantitative PCR analysis of the FLRT3 gene expression level in dorsal root ganglion cells harvested from neuropathic pain model rats.
Figure 2:
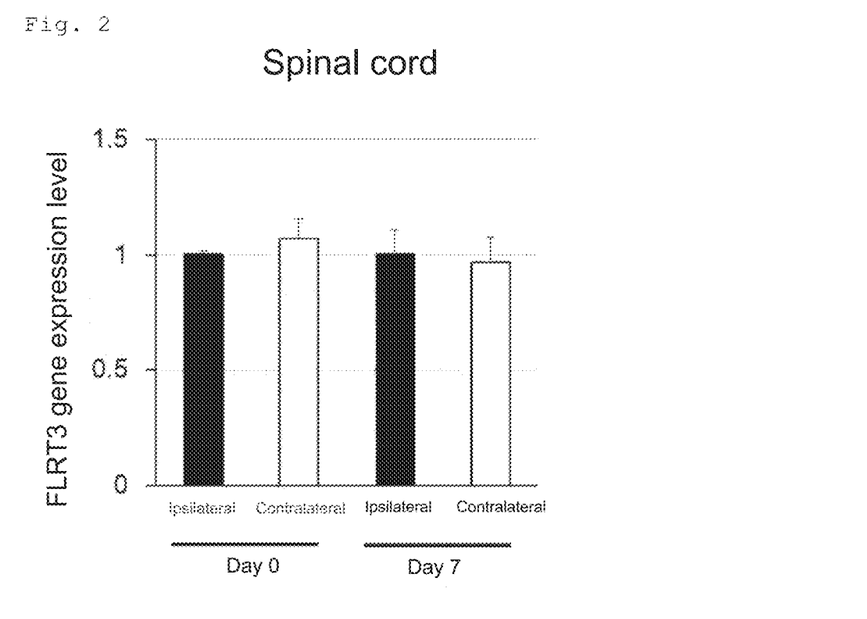
FIG. 2 shows the results of quantitative PCR analysis of the FLRT3 gene expression level in the spinal cord harvested from neuropathic pain model rats.

The results of the quantitative PCR analysis of the dorsal root ganglion cells are shown in FIG. 1, and the results of the quantitative PCR analysis of the spinal cord tissue (lumbar enlargement) are shown in FIG. 2. As is clear from FIG. 1, FLRT3 gene expression significantly increased in the dorsal root ganglion cells on the side ipsilateral to the injury ( $p<0.01$ vs Day 0). In contrast, no significant increase in the FLRT3 gene expression was observed in the spinal cord on the side ipsilateral to the injury, as is clear from FIG. 2**. These results show that, under neuropathic pain conditions, FLRT3 gene expression is increased in the dorsal root ganglion cells, but not in the spinal cord.

(2) FLRT3 Protein Expression Level in Neuropathic Pain Model

Next, the change in FLRT3 protein expression under neuropathic pain conditions was analyzed by western blotting. At 0 and 7 days after the production of the neuropathic pain model, spinal cord tissue (lumbar enlargement) and dorsal root ganglion cells on the side ipsilateral to the injury were separately harvested from each model rat. Similarly, the contralateral spinal cord tissue (lumbar enlargement) and dorsal root ganglion cells were also harvested. After the proteins from each sample were subjected to SDS-PAGE, the expression levels of FLRT3 and beta-actin were measured.

Figure 3:
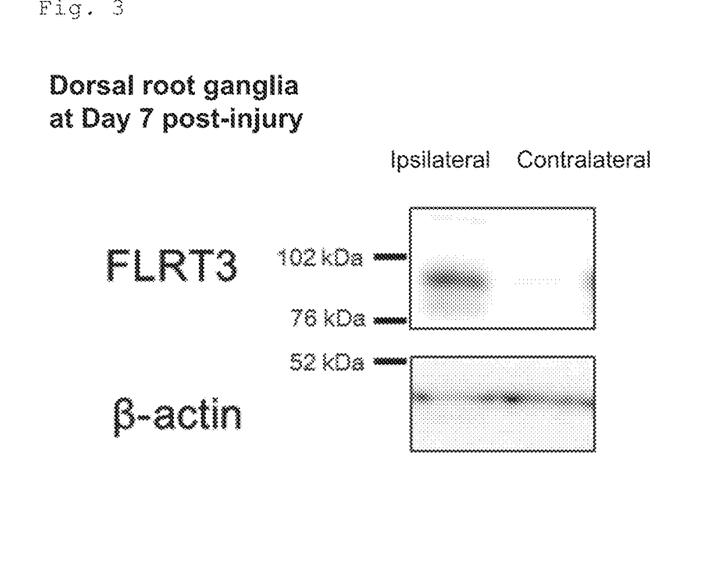
FIG. 3 shows the results of western blotting analysis of the FLRT3 protein expression level in dorsal root ganglion cells harvested from neuropathic pain model rats.
Figure 4:
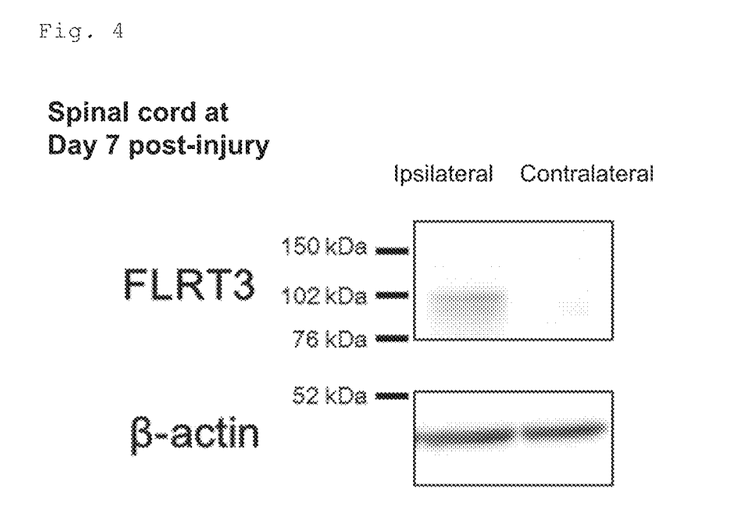
FIG. 4 shows the results of western blotting analysis of the FLRT3 protein expression level in the spinal cord harvested from neuropathic pain model rats.

The results of the western blotting analysis of the dorsal root ganglion cells on day 7 post-injury are shown in FIG. 3, and the results of the western blotting analysis of the spinal cord tissue (lumbar enlargement) on day 7 post-injury are shown in FIG. 4. As is clear from FIG. 3, the FLRT3 protein expression in the dorsal root ganglion cells on day 7 post-injury was increased on the side ipsilateral to the injury. As is clear from FIG. 4, the FLRT3 protein expression in the spinal cord on day 7 post-injury was also increased on the side ipsilateral to the injury.

Considering all the results collectively, since the FLRT3 gene expression level in the spinal cord was not increased by nerve injury as shown in the above-described quantitative PCR analysis, the increase in FLRT3 protein expression in the spinal cord after the injury is probably due to the axonal transport of FLRT3 expressed in sites other than the spinal cord, in particular dorsal root ganglion cells, to the spinal cord.

Figure 5:
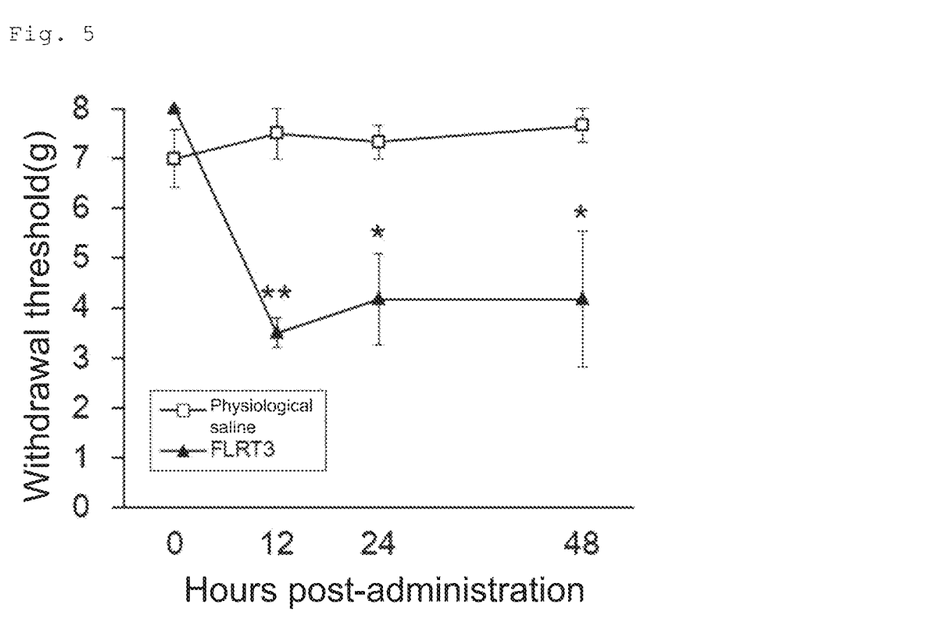
FIG. 5 shows the change in withdrawal threshold in rats in the von Frey filament test after intrathecal administration of FLRT3 protein.

(3) Potentiation of Nociceptive Response by Intrathecal Administration of FLRT3 Protein In order to clarify the function of FLRT3 protein in the spinal cord, the change in the nociceptive response after intrathecal administration of FLRT3 protein was examined. The von Frey filament test was performed at 12, 24 and 48 hours post-administration to examine the change in withdrawal threshold. The results are shown in FIG. 5. As is clear from FIG. 5, the FLRT3 protein-administered animals showed a gradual reduction in withdrawal threshold after the administration. The degree of the reduction in withdrawal threshold in the FLRT3 protein-administered rats was significantly larger than that in the control rats at 12, 24 and 48 hours post-administration (Tukey-Kramer test, ** $p<0.01$, * $p<0.05$).

The above results indicate that FLRT3 functions to potentiate nociceptive response in the spinal cord of adult animals, thus causing pain.

Example 2: Suppression of Nociceptive Response by Anti-FLRT3 Antibody

In order to clarify whether anti-FLRT3 antibody has analgesic effect on neuropathic pain, an anti-FLRT3 antibody (R&D, AF2795) was intrathecally administered to model rats which had developed pain, and pain-related behavior in the rats was examined. First, a polyethylene tube was inserted into the intrathecal space in 8-week-old male Wistar rats. One week after the intubation, the sciatic nerve of the left hind limb of each rat was partially ligated to produce a neuropathic pain model. Seven days after the pain model production, the von Frey filament test was performed to confirm the reduction in withdrawal threshold (i.e., the development of mechanical allodynia) in each rat. The anti-FLRT3 antibody was dissolved at a concentration of 1 µg/µL in physiological saline, and 30 µL of this solution was infused from the outer end of the indwelling intrathecal polyethylene tube. Meanwhile, the same volume of a control goat IgG solution (1 µg/µL) was administered to control group animals. After the administration, the outer end of the tube was closed and the skin incision was sutured. The von Frey filament test was performed at 12, 24 and 48 hours post-administration to examine the change in withdrawal threshold in the hind limb ipsilateral to the injury.

Figure 6:
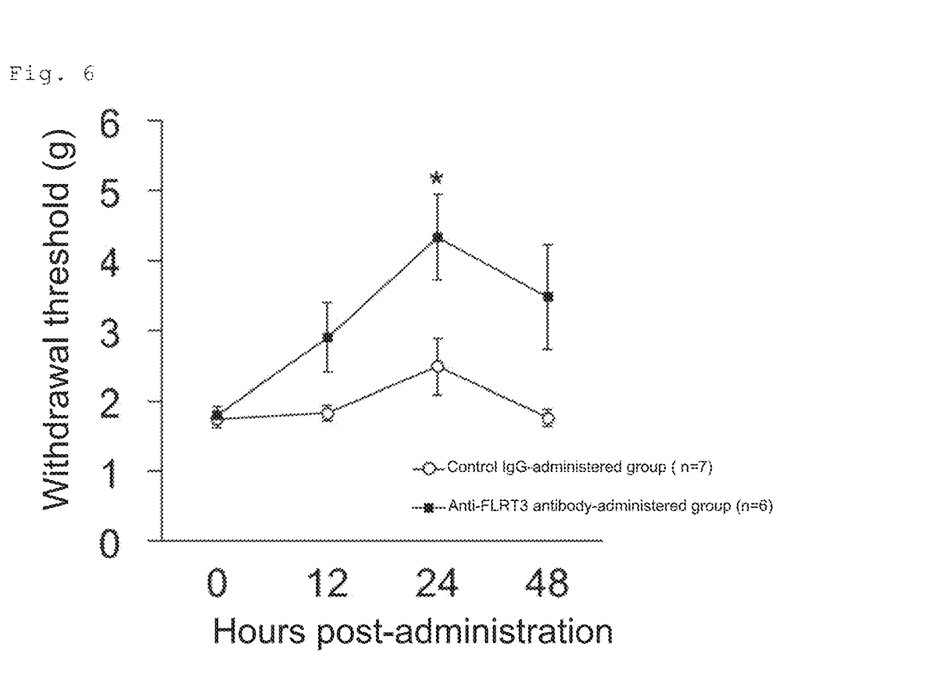
FIG. 6 shows the time-course change in withdrawal threshold in the hind limb ipsilateral to injury in neuropathic pain model rats in the von Frey filament test after intrathecal administration of anti-FLRT3 antibody.

The results are shown in FIG. 6. As shown in FIG. 6, the withdrawal threshold in the anti-FLRT3 antibody-administered group was higher than that in the control group. In particular, significant difference was observed at 24 hours post-administration as compared with the control group (Tukey-Kramer test, * $p<0.05$). These results show that the intrathecal administration of the anti-FLRT3 antibody exerts analgesic effect on neuropathic pain.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A screening method for a pain suppressor substance, the method comprising:
   bringing a test substance into contact with FLRT3 and Unc5B;
   assessing FLRT3 binding to Unc5B;
   determining whether or not the test substance inhibits FLRT3 binding to Unc5B; and
   identifying the test substance as said pain suppressor substance if the test substance inhibits FLRT3 binding to Unc5B.

2. A method for the inhibition or treatment of pain in a subject, comprising:
   administering an effective amount of a pain suppressor substance to said subject, wherein said pain suppressor substance comprises a nucleic acid comprising a sequence that inhibits FLRT3 expression.

3. A method for the inhibition or treatment of pain in a subject, comprising:
   administering an effective amount of a pain suppressor substance to said subject, wherein said pain suppressor substance comprises a peptide comprising a sequence that inhibits an interaction between FLRT3 and Unc5B, and wherein said pain suppressor substance is an anti-FLRT3 antibody.

4. A method for the inhibition or treatment of pain in a subject, comprising:
   administering an effective amount of a pain suppressor substance to said subject, wherein said pain suppressor substance comprises a peptide comprising a sequence that inhibits an interaction between FLRT3 and Unc5B, wherein the subject has peripheral neuropathy-associated pain.

5. The method according to claim 4, wherein an antibody is administered to said subject.

6. The method according to claim 4, wherein the pain suppressor substance inhibits FLRT3 transport to the spinal cord, inhibits FLRT3 binding to Unc5B, or specifically binds to FLRT3.

7. The method according to claim 4, wherein the pain suppressor substance is contacted with dorsal root ganglion cells, dorsal root fibers or axon terminals of dorsal root ganglion neurons of said subject.

* * * * *